United States Patent [19]

Khan

[11] Patent Number: 5,317,901
[45] Date of Patent: Jun. 7, 1994

[54] NONDESTRUCTIVE TEST FOR COATED CARBON-CARBON COMPOSITE ARTICLES

[75] Inventor: Abdus S. Khan, Palm Beach Gardens, Fla.

[73] Assignee: United Technologies Corporation, Hartford, Conn.

[21] Appl. No.: 807,420

[22] Filed: Dec. 10, 1985

[51] Int. Cl.⁵ .............................. G01M 3/02
[52] U.S. Cl. ........................ 73/45.5; 73/52; 73/104; 427/8
[58] Field of Search ............... 427/2, 9, 10; 73/159, 73/45.5, 52, 104

[56] References Cited

U.S. PATENT DOCUMENTS

| | | | |
|---|---|---|---|
| 1,613,962 | 1/1927 | Schworetzky . | |
| 2,055,568 | 9/1936 | Wilsdorf | 73/45.5 |
| 2,316,842 | 4/1943 | Coleman | 73/45.5 |
| 2,340,940 | 2/1944 | DeForest | 73/104 |
| 2,407,945 | 9/1946 | Bennett, Jr. | 73/45.5 |
| 2,633,740 | 4/1953 | Howe et al. | 73/45.5 |
| 2,846,872 | 8/1958 | McAdams et al. | 73/45.5 |
| 2,961,869 | 11/1960 | Bagno | 73/45.5 |
| 3,064,466 | 11/1962 | Liers | 73/45.5 |
| 3,590,256 | 6/1971 | Neeff | 73/45.5 |
| 3,592,047 | 7/1971 | Carleton | 73/45.5 |
| 4,506,544 | 3/1985 | Shimizu | 73/45.5 |

FOREIGN PATENT DOCUMENTS

| | | | |
|---|---|---|---|
| 58-123439 | 7/1983 | Japan | 73/45.5 |
| 513288 | 6/1976 | U.S.S.R. | 73/45.5 |
| 813152 | 3/1981 | U.S.S.R. | 73/45.5 |

Primary Examiner—John F. Terapane
Assistant Examiner—Eric Jorgensen
Attorney, Agent, or Firm—James M. Rashid

[57] ABSTRACT

A method for determining whether surface connected, through thickness defects exist in a coated carbon-carbon composite article. The method involves the immersion of the coated article in a low viscosity liquid; if a stream of bubbles rises from the surface of the coating, such bubbles indicate the existence of at least one surface connected, through thickness defect in the coating.

3 Claims, No Drawings

NONDESTRUCTIVE TEST FOR COATED CARBON-CARBON COMPOSITE ARTICLES

TECHNICAL FIELD

This invention relates to coatings for carbon base materials. More particularly, the invention relates to a nondestructive test for detecting surface connected through thickness defects in coated carbon-carbon composite articles.

BACKGROUND ART

Carbon-carbon composites are a unique class of materials whose elevated properties make them attractive for various aerospace applications. Anticipated applications of carbon-carbon composites in gas turbine engines include components such as exhaust nozzle flaps and seals, and tail cones. The materials are composites, although in general, all of the composite elements are carbon, in its various allotropic forms. Carbon-carbon materials are produced from organic precursor fibers, such as polyacrylonitrile, rayon, or pitch. Such fibers are usually produced in bundles (yarn), often by an extrusion process. The precursor fibers are heated in an inert atmosphere to pyrolyze or carbonize them, and may then be heated to a higher temperature (usually above about 2,000° C.) to form graphite fibers. These graphite fibers may then be layed down, woven, or interleaved to form what are referred to as 1D, 2D, 3D, etc., structures where D stands for direction (i.e., in a 2D structure, fibers are layed in two, usually orthogonal, directions).

These woven structures may then be impregnated with a pitch or resin material which, by the application of heat, is converted to carbon which acts as the matrix for the composite. Hot pressing may be employed to obtain a more dense structure. Repeated impregnation steps may also be used to increase the density of the product being fabricated. In general, the product never achieves 100% theoretical density, i.e., it is porous. The density of some carbon-carbon components is in the range of about 1.3-1.75 grams per cubic centimeter (g/cc).

The finished product is usually at least 90-95% carbon, but by virtue of the fiber alignment and other processing details, has exceptional mechanical properties when compared with other carbon type materials such as monolithic graphite. The mechanical properties of carbon-carbon composite materials are constant, or even increase slightly, with temperature exposure up to about 2,000° C. This temperature capability makes carbon-carbon materials exceptionally attractive for various aerospace applications.

One of the few drawbacks of carbon-carbon materials is their susceptibility to oxidation degradation at temperatures above about 340° C. Various coatings have been developed which protect carbon-carbon substrates from oxidation. To be fully protective of the carbon-carbon substrate, the coating must fully encapsulate the component, viz., there must be no gaps in the coating, or defects which extend through the thickness of the coating and to the substrate. In applications where the coated component will be exposed to severe cyclic conditions (temperature and/or stress), a duplex, or two layer, coating system may be used to insure that the substrate is sufficiently protected from the environment. Some of the useful coatings for carbon-carbon components are disclosed in, e.g., U.S. Pat. Nos. 4,465,777, 4,472,476, 4,476,164, 4,476,178, and 4,544,412, all of which are incorporated by reference. Glass-type coating systems for carbon-carbon components have also been proposed.

Cracks in single layer coating systems, as well as in two layer coating systems have been observed. While a majority of these cracks do not extend to the carbon-carbon substrate, some do. Catastrophic oxidation of the carbon-carbon substrate may occur when oxygen, moving through these defects, comes in contact with the substrate at elevated temperatures. Theoretically, any defect which is larger than the size of the oxygen atom is large enough to permit contact of oxygen with the substrate, which would begin the oxidation process. However, the rate at which oxygen moves through these very small through thickness defects is slow, and it is probably not until the component experiences stress at high temperatures that these defects increase to a size at which rapid oxygen diffusion, and therefore, rapid oxidation degradation, occurs. It is believed that the through thickness defect size which can result in rapid oxidation may be as small as about 15-150 microns. For the purposes of this specification and attached claims, defects which extend from the outer surface of the coating and through the entire thickness of the coating to the carbon-carbon substrate are termed through thickness defects.

Metallographic and X-ray techniques have heretofore been used to detect the existence of defects in coatings applied to carbon-carbon materials. However, as is known to those skilled in the art, such techniques are time consuming. As a result, newer and faster techniques are constantly being sought to determine the existence of such defects.

Numerous prior art patents teach methods for the nondestructive detection of cracks and other defects in various types of materials. See, e.g., U.S. Pat. Nos. 1,370,347, 1,613,962, 2,055,568, 2,316,842, 2,407,945, 3,064,466, 3,590,256, and 3,592,047. However, each of these patents is concerned with the examination of pressurized or air-tight containers, or, alternatively, the examination of articles using pressurized liquid. In both of these types of techniques, cracks are identified by air bubbles which rise from the surface of the article being examined. However, these techniques are complicated, and often use bulky equipment; they are not felt suitable for the examination of carbon-carbon composite materials, especially aircraft engine components, some of which can be several feet in length and breadth.

Thus, what is needed in the art is a fast, yet simple method for detecting very small, surface connected defects in coatings applied to carbon-carbon materials.

DISCLOSURE OF THE INVENTION

According to the present invention, a method for detecting surface connected, through thickness defects in a coating applied to a porous carbon-carbon composite article comprises the steps of cleaning the coated article to remove any debris from the surface of the coating, immersing the coated article in a substantially clear liquid, and visually observing for air bubbles rising from the surface of the coating, the bubbles being indicative of the existence of at least one surface connected, through thickness defect in the coating.

For coated carbon-carbon articles, the resistance to oxidation degradation is determined by the condition of the coating. If there are no through thickness cracks in the coating, the oxidation resistance of the article will be good, and accordingly, the article will exhibit useful high temperature behavior. If, however, there are through thickness cracks in the coating, the oxidation resistance of the article will be poor, and will exhibit non-useful high temperature behavior. The present invention, an easy and quick method for determining the existance of through thickness cracks in coatings applied to carbon-carbon substrates represents a significant advancement in the characterization of these coatings.

The foregoing and other features and advantages of the present invention will become more apparent in the light of the following detailed description of the preferred embodiments thereof.

BEST MODE FOR CARRYING OUT THE INVENTION

A new technique for inspecting coatings applied to carbon-carbon components has been developed which is fast, simple to perform, and provides results which have been correlated with the results obtained in furnace oxidation tests. Tests have shown that this new technique is useful in examining coatings such as SiC, $Si_3N_4$, SiC+glass duplex coatings, SiC+$Si_3N_4$ duplex coatings, and variations thereof, applied to carbon-carbon composite materials. In this technique, the coated carbon-carbon specimen is first cleaned of any surface debris such as dust or oil, and then immersed in a substantially clear liquid such as water, acetone, or isopropyl alcohol. If there are any surface connected, through thickness defects in the coating, the liquid will at first displace the air in the defect, and bubbles will be seen rising from the surface of the coated component. Then, as the liquid further infiltrates the defect and eventually reaches the porous carbon-carbon substrate, it will displace the air in the substrate, resulting in the generation of more bubbles which will be seen rising from the surface of the coated component.

It is believed that the specific choice of the liquid used in these tests is not critical. It should be substantially clear to allow for visible inspection of the test piece when the test piece is immersed therein. The liquid must be able to infiltrate the fine cracks which may exist in the coatings, so it must have a relatively low viscosity. Acceptable results have been achieved using water, acetone, and isopropyl alcohol, although it is believed that equally acceptable results may be achieved with other low molecular weight alcohols. One advantage of using alcohol or other such volatile liquids is that they are easily evaporated from the coated component by first drying at room temperature for about 30 minutes, followed by heating at about 100° C. for 30 minutes and then at about 200° C. for about 60 minutes. Such a cycle leaves no residual liquid on the component. This is especially important, since if residual liquid were present in a defect in the coating, and the coated component were then installed in a jet engine, the rise in temperature during startup of the engine would cause vaporization of the liquid, which could result in delamination of the coating from the substrate, or even delamination of the graphite fibers.

As an example of the use of the invention, a carbon-carbon test piece having a SiC+glass duplex coating was examined. The coating thickness was about 0.2–0.3 mm. Visual examination of the specimen revealed that there were some defects evident on the surface of the coating. This is not unusual; such defects may form during the cool-down period following the elevated temperature coating process. However, the visual examination was not able to determine the depth or significance of the defects. To determine whether any of these defects extended through the thickness of the duplex coating, the specimen was first cleaned in isopropyl alcohol for about 10 minutes. Then, the cleaned specimen was immersed in a beaker of isopropyl alcohol at room temperature. Shortly after immersion, a fine stream of air bubbles was observed rising from the surface of the coating. The stream of bubbles continued for about 10 seconds, which was indicative of the existence of a through thickness defect in the coating. When the bubbles ceased, the specimen was removed from the alcohol, and dried first in air for about 30 minutes, then at about 100° C. for another 30 minutes, followed by 200° C. for 1 hour.

Cyclic oxidation testing was then conducted to verify the observation made during the immersion test, i.e., that the coating had at least one through thickness defect. The oxidation testing comprised five 1 hour cycles at 1,000° F., followed by five 1 hour cycles at 1,200° F. The specimen was weighed after each 1 hour cycle, as well as visually inspected. Weight loss and physical degradation of the specimen was observed during this testing, indicative of oxidation of the carbon-carbon substrate. The physical degradation was most severe in the area where bubbles were observed rising from the surface of the coating during the immersion test, which confirmed the existence of a through thickness defect in the coating.

In another test, a SiC+glass duplex coated carbon-carbon specimen was cleaned and then immersed in a beaker of isopropyl alcohol at room temperature. No bubbles were observed rising from the surface of the specimen. Cyclic oxidation testing of this specimen (at the same test conditions as described above) revealed satisfactory performance, i.e., no rapid physical degradation or weight loss.

In yet another test, a SiC+glass duplex coated carbon-carbon specimen was cleaned and then immersed in a beaker of water at room temperature. A stream of bubbles was observed rising from the surface of the specimen; during subsequent oxidation testing, the specimen suffered severe localized oxidation associated with the previously detected defect.

In the above-described tests, any bubbles which rose from the surface of the coating were detected visually. However, it is within the scope of the present invention that bubbles may be detected in an automated fashion, by providing appropriate means for detecting the bubbles. Such an automated system may also permit the use of liquids which are not necessarily transparent to the human eye.

Also in these tests, only duplex coating systems (i.e., two coating layers) were examined. However, it is apparent that the present invention will be equally useful in examining single layered coatings, as well as coating systems having two or more coating layers. In the latter type of coating systems, a through thickness defect is considered to exist if defects in the individual layers are aligned so as to allow for the diffusion of oxygen therethrough to the carbon-carbon substrate.

It is believed that this inspection method will be most useful as a quality control tool for identifying defective and nondefective, as-coated, carbon-carbon articles. However, it should also be useful in determining the existence of through thickness defects in service operated articles.

The present invention will only identify through-thickness defects. While there may be some defects which do not extend through the entire coating thickness, these defects do not apparently act as initiating sites for oxidation attack of the substrate. When immersed in the liquid, there are little or no bubbles which rise from these defects, because the defects are so shallow and the liquid cannot penetrate to the porous carbon-carbon substrate and displace the quantity of air necessary to form a stream of bubbles.

Thus, the present invention provides a fast, simple and reliable technique for identifying defective coatings on carbon-carbon articles, i.e., coatings which have through thickness defects therein. This is especially important in the fabrication of components used in severe operating environments such as gas turbine engines. Such components may undergo catastrophic failure if any through thickness coating defects exist. Since it is believed that the actual engine component should be inspected, rather than merely inspecting a test specimen, this immersion test should be very valuable in the identification of usable and nonusable coatings. If the coating is identified as being defective, another layer of the coating may be applied to the component.

Although the invention has been shown and described with respect with a prefered embodiment thereof, it should be understood by those skilled in the art that other various changes and omissions in the form and detail thereof may be made therein without departing from the spirit and scope of the invention.

I claim:

1. In a gas turbine engine component made of a carbon-carbon substrate and having a coating on the surface of the substrate which encapsulates the substrate, a method for detecting cracks in the coating which extend from the surface of the coating to the substrate, the method comprising the steps of cleaning the coating surface, immersing the component in a low viscosity liquid, and observing for a stream of air bubbles rising from the coating surface, said bubbles indicating at least one crack which extends completely through the coating to the substrate.

2. In a carbon-carbon gas turbine engine component having a 0.01–0.75 mm thick coating thereon which encapsulates the component, a method for detecting cracks in the coating which extend completely through the coating, the method comprising the steps of cleaning the coating surface, immersing the component in a low viscosity liquid, and observing for a stream of bubbles rising from the coating surface while the liquid is at atmospheric conditions, said bubbles indicating at least one crack which extends completely through the coating.

3. The method of claim 2, wherein the liquid is selected from the group consisting of water and the low molecular weight alcohols.

* * * * *